United States Patent
Fauske et al.

[11] Patent Number: 6,157,009
[45] Date of Patent: Dec. 5, 2000

[54] ADVANCED REACTIVE SYSTEM SCREENING TOOL

[75] Inventors: Hans K. Fauske, Hinsdale, Ill.; Pedro Tellez, Zaragoza, Spain; Jose Angel Pena, Zaragoza, Spain; Jesus Santamaria, Zaragoza, Spain; Maria Estrel Marco, Zaragoza, Spain

[73] Assignee: Fauske and Associates, Inc., Burr Ridge, Ill.

[21] Appl. No.: 09/175,594

[22] Filed: Oct. 20, 1998

Related U.S. Application Data

[60] Provisional application No. 60/098,003, Aug. 26, 1998.
[51] Int. Cl.$^7$ .................................................. H05B 1/02
[52] U.S. Cl. .................. 219/497; 374/1; 374/31
[58] Field of Search .................. 219/482, 490, 219/492, 494, 497, 498, 499, 509, 510, 516; 374/1, 2, 3, 31, 32, 33, 34, 35, 36, 37, 38, 39, 40, 41, 42; 422/130; 436/34

[56] References Cited

U.S. PATENT DOCUMENTS

| | | | |
|---|---|---|---|
| 4,398,836 | 8/1983 | Sitek | 374/38 |
| 4,434,342 | 2/1984 | Schubring | 219/497 |
| 4,456,389 | 6/1984 | Regenass et al. | 374/31 |
| 4,670,404 | 6/1987 | Swift et al. | |
| 4,846,584 | 7/1989 | Burch et al. | 374/31 |
| 4,901,257 | 2/1990 | Chang et al. | 374/1 |
| 5,098,196 | 3/1992 | O'Neill | 219/497 |
| 5,229,075 | 7/1993 | Fauske | |
| 5,363,471 | 11/1994 | Jones | 219/492 |
| 5,672,289 | 9/1997 | O'Neill | 219/497 |
| 5,793,022 | 8/1998 | Klinck et al. | 219/497 |
| 5,824,886 | 10/1998 | Selby et al. | 219/523 |

*Primary Examiner*—Teresa Walberg
*Assistant Examiner*—Fadi H. Dahbour
*Attorney, Agent, or Firm*—Tom R. Fitzsimons

[57] ABSTRACT

The present invention comprises a calorimeter apparatus having a very low thermal mass ratio of test cell to test sample so as to minimize heat sink effects on the test sample during a chemical reaction. The heater control algorithm of the present invention comprises a calibration stage in which the heater is tuned to the particular test conditions at hand, and a test stage in which the heater may control the sample in a ramping mode and in an adiabatic mode. Because the sample may be tested in an adiabatic mode, greatly improved sensitivity in detection of reaction onset may be achieved, and measured data is truly adiabatic and need not be adjusted for analysis. The present invention further comprises a calorimeter apparatus having a foam detector for detecting the presence of foam in the test sample.

14 Claims, 13 Drawing Sheets

ADVANCED REACTIVE SYSTEM SCREENING TOOL

CROSS REFERENCE

The present application claims the benefit of U.S. Provisional Application No. 60/098,003 filed Aug. 26, 1998.

FIELD OF THE INVENTION

The present invention relates to laboratory calorimeter devices. More particularly, the present invention relates to adiabatic calorimeter devices that may be useful in the characterization of runaway chemical reactions.

BACKGROUND OF THE INVENTION

It is well known in the art to use laboratory reaction calorimeter devices to obtain design basis data for designing chemical process relief systems. Data obtained include adiabatic rates of temperature and pressure rise for very fast, runaway type reactions. These devices generally operate by heating a test sample contained in a test cell until a threshold of a reaction is detected. Once a reaction is under way, heaters are manipulated to balance heat losses from the test sample so that the sample may remain adiabatic as it reacts.

There are presently available several reaction calorimeters useful for the study of runaway reactions. An example includes the device of Fauske's U.S. Pat. No. 4,670,404. While this device offers general utility, it may tend to be a difficult, expensive, and cumbersome device to operate and maintain due to its relatively complicated configuration. A less expensive, simpler reaction calorimeter useful for obtaining relief system design basis data is described in detail in Fauske's later U.S. Pat. No. 5,229,075, the teachings of which are herein incorporated by reference.

In order to offer a simpler, less expensive, and easier to use system, the device disclosed in the '075 patent utilizes a single heater, single temperature probe configuration, as opposed to a plurality of heaters and temperature probes of prior devices. Although the '075 device satisfied a need for a relatively uncomplicated tool, it presents several problems. Primary among these problems is the mode of heating a test sample.

To run a test, the '075 device simply ramps a sample temperature at a constant temperature rise ramp rate. If a reaction should occur during that temperature ramping, the '075 device will continue to provide background ramping so as to minimize any heat losses from the cell.

By way of example, a sample may be ramped at a rate of 1° C./min to a temperature of 300° C. If a reaction is encountered at 200° C., the reaction heat will cause the sample to heat faster than the prescribed 1° C./min. In order to insure that heat is not being lost from the sample, the '075 device will continue to input the constant 1° C./min. ramp rate. Thus the actual heat rates observed and measured are a combination of the reaction heat and the device ramping heat. To obtain actual heat rates due to reaction energy, the device ramp rate must be subtracted out of the observed rate data. Such a subtraction disadvantageously introduces numerous approximations, calculations, and associated uncertainty to data interpretation.

In addition to rate data, the onset temperature of a reaction at which an exotherm begins to occur is of great importance to relief system designers and others. Because of its simple mode of operation, the '075 device must heat a sample at a constant ramp rate to search for an exothermic reaction. Its method of heater control is not capable of holding a sample in an adiabatic state to search for an exotherm. Because the '075 device is heating a sample at a constant ramp rate, reaction heat will not be evident until that reaction heat is substantial enough to cause the temperature rise rate to exceed the background ramp rate.

For instance, if a sample is being heated at an imposed rate of 1° C./min. by the device heater, an exotherm that may occur will not be evident until it causes the observed rate to rise some amount over 1° C./min. By this time, however, the reaction has been under way for some time. The heating control scheme of the '075 device therefor causes a lack of sensitivity in detection of reaction onset. In order to estimate an onset of reaction temperature when using this heating control scheme, it is necessary to subtract out the background imposed ramp rate from the observed heat rate. Such a data treatment requires several approximations, calculations, and introduces uncertainty.

Other calorimeters are capable of heating a sample such that observed temperature rise rates are due only to reaction heat, and are able to hold samples in an adiabatic state to detect exothermic reaction onset at very low levels. Prior art devices that have these capabilities, however, require a relatively expensive, complicated design with a plurality of heaters and temperature probes. No prior art devices have been able to achieve satisfactory heater control for accurate measurement of rates and onsets in combination with a relatively simple and inexpensive general configuration with only a single heater and a single temperature probe.

The method of heater control of prior art calorimeters such as the '075 device that use a single heater and thermocouple also have a problematic manner of heating a sample when a reaction is not occurring. These devices calculate the amount of heater power to apply to ramp a sample based on a stored calibration algorithm that relates sample temperature to heater power. This calibration algorithm assumes a sample mass, specific heat, and heat loss model. Sample mass may be somewhat predictable and controllable by a user. Sample specific heat, however, is very unpredictable. For a typical organic material, for instance, a specific heat may be expected to be approximately 0.5 cal/(gm ° C.), while for an aqueous material the specific heat would be expected to be twice this amount. Further, the heat loss model may vary considerably from test to test, particularly as the test pressure is varied.

These variances often result in the control algorithm of these prior art devices to apply inaccurate amounts of heat, resulting in imposed ramp rates of the sample that can vary greatly from the desired imposed rate. It is not uncommon for heat rates to vary by a factor of 2 or more when using the heater control scheme of the '075 device, for instance. In some cases, the errors resulting from incorrect calibration assumptions may lead to a sample ramp rate that is not constant but increases over time, which may be mistakenly interpreted by a user as a reaction exotherm. Likewise, the ramp rate may decrease over time, potentially masking an exotherm.

In addition to problems with methods of heater controls, an additional problem that all prior art calorimeter devices share is a lack of any means for characterizing the flow regime of a material. In particular, the flow regime of a material under given reaction conditions may be generally characterized as foamy or non-foamy. As its name suggests, foamy system behavior is generally characterized as a tendency for the liquid level to swell or foam as a reaction occurs and vapor or gas is generated in a liquid bulk. A common example of foamy behavior would be soapy water as air is blown into it; a great deal of foam results. A non-foamy system, on the other hand, does not tend to produce significant liquid level swell or foam during a runaway excursion. Water without any soap additives, for instance, does not foam appreciably as air is blown into it.

No known prior art calorimeter systems or other bench scale systems are equipped to make flow regime characterizations, such as a determination of whether a reaction under given conditions may be characterized as foamy or non-foamy. Further, it is not possible to predict whether a material may be characterized as foamy or non-foamy when under runaway reaction conditions based on physical property data alone. Currently, the only method by which flow regime characterization such as foamy or non-foamy classification may be made is through visual observation. As this practice is not safe or practical for a reaction under runaway conditions, observation is not useful means of obtaining relief system design basis data.

In terms of relief system design, the characterization of a system as foamy or non-foamy is of critical importance. A foamy system presents a much more challenging system to accommodate under runaway conditions than does a non-foamy system. A foamy system generally requires larger overall capacity, with larger diameter vent piping and larger capacity down stream relief system components. Without such accommodations foamy systems may result in pressure rises that exceed vessel design pressures and cause vessel failure. As there is presently no known available practical method or apparatus for determining whether a reactive system is foamy or non-foamy, current relief system design practice is to generally assume all systems are foamy and to thus design overly conservative relief systems in many cases.

Further, for a given foamy system, there are no calorimeter devices capable of determining at what point during a reaction foamy behavior begins. Such information would be of great value, as a relief system could potentially be designed to accommodate the reaction during its non-foamy stage, thereby resulting in a less extensive, less costly system.

In conclusion, an unresolved need in industry exists for a method and apparatus for characterizing a material's flow regime characteristics under runaway conditions.

Further, there is an unresolved need for a reaction calorimeter useful for obtaining relief system design basis data that combines a relatively simple, low cost design with a reliable method of heater control.

There is also an unresolved need for a simple reaction calorimeter useful for obtaining relief system design basis data that offers consistent and accurate imposed heat rates.

There is also an unresolved need for a calorimeter tool which uses a relatively simple, single heater and single temperature probe configuration that does not require searching for an exothermic onset temperature during ramping.

OBJECTS OF THE INVENTION

It is an object of the invention to provide a relatively simple reaction calorimeter useful for obtaining relief system design basis data that utilizes an accurate method of heater control that is based on the particular specific heat, mass, and heat loss model of the present individual test sample.

It is a further object of the invention to provide a relatively simple reaction calorimeter useful for obtaining relief system design basis data that is capable of measuring rates of temperature rise that directly reflect reaction heat and do not require subtracting out of a background ramp rate.

It is a further object of the invention to provide a relatively simple reaction calorimeter useful for obtaining relief system design basis data that is capable of detecting the onset of an exothermic reaction from a substantially adiabatic state.

It is a still further object of the invention to provide a method and apparatus for characterizing a material's flow regime as foamy or non-foamy during a runaway reaction.

SUMMARY OF THE INVENTION

The apparatus of the invention generally includes a sealable containment vessel for providing a controlled atmosphere having pressure measurement means, a test cell with thermal insulation disposed in the containment vessel for containing the test sample material, heater means for heating the test sample material, temperature measurement means for measuring the temperature of the test sample material, means for agitating the test sample material, and data acquisition means for recording temperature and pressure data. As heretofore described the apparatus is that as is generally known in the art. In order to satisfy the unresolved needs described herein, however, the apparatus of the present invention further comprises novel heater control means for controlling the heater, and foam detection means.

The preferred method of heater control of the present invention comprises a computer program running on a microprocessor based computer in communication with the apparatus of the invention. The method of heater control of the present invention generally comprises a calibration stage and a test stage. In the calibration stage, the heater is controlled by a control loop to tune itself for the particular test sample mass, sample specific heat, and heat loss model of the test at hand. The heater is tuned under two performance models, a ramping mode in which the sample temperature is raised, and an adiabatic mode in which the sample is held in an approximate adiabatic state. After being tuned, precise relationships are derived for the test sample and conditions at hand that may be used to control the heaters during the test stage. In this manner the method of heater control of the present invention is calibrated for the particular conditions of the test at hand, providing for greatly improved performance over prior art devices that relied upon stored factors that assumed test conditions.

Using the respective relationships derived in the calibration stage, the subsequent test stage of the method of heater control of the present invention allows for holding a sample in a substantially adiabatic state in addition to accurately ramping a sample at a desired imposed ramp rate. By holding the sample in a substantially adiabatic state, the onset of exothermic reactions can be detected with much greater accuracy than was possible with prior art devices. Further, because the sample is in a substantially adiabatic state, measured rates of temperature rise that are measured during an exothermic reaction do not include a background imposed rate of temperature rise which must be subtracted out. This reduces the effort required in using data of the present invention as compared to the data of prior art devices, and also reduces uncertainty in the data as compared to the data of prior art devices.

Test results using the method of heater control of the present invention with relatively simple calorimeter configurations having a single heater and a single temperature probe show great improvement over prior art control algorithms with the same simple calorimeter configuration.

The present invention further comprises foam detection means for detecting the presence of foam in a sample being tested in a calorimeter. The foam detection means of the present invention generally comprise a detector placed above the surface level of a test sample. As foam rises from the sample it will come into contact with the foam detector. The foam detector will then send a signal to a data recording medium that records the temperature, time, and pressure at which foam was detected.

The preferred foam detector comprises a probe with a heater for heating the probe surface, and a thermocouple attached to the probe surface for measuring its temperature. The probe is of relatively low thermal mass, so that the surface temperature will change rapidly when contacted with cooling media. When the probe surface is in a gaseous environment, the surface is heated to an elevated temperature substantially above the predicted tempering temperature of the components of the liquid being tested. When foam comes in contact with the heated surface, the liquid component of the foam quickly cools the surface of the probe through latent heat of vaporization effects as the liquid turns to vapor on contact with the heated surface. Consequently, the probe surface temperature rapidly falls to a temperature approximately corresponding to the tempering temperature of the liquid component of the foam due to evaporative cooling effect. The temperature of the probe surface at this time should correspond to the measured temperature of the liquid.

The above brief description sets forth rather broadly the more important features of the present disclosure so that the detailed description that follows may be better understood, and so that the present contributions to the art may be better appreciated. There are, of course, additional features of the disclosure that will be described hereinafter which will form the subject matter of the claims appended hereto. In this respect, before explaining the several embodiments of the disclosure in detail, it is to be understood that the disclosure in not limited in its application to the details of the construction and the arrangements set forth in the following description or illustrated in the drawings. The present invention is capable of other embodiments and of being practiced and carried out in various ways, as will be appreciated by those skilled in the art. Also, it is to be understood that the phraseology and terminology employed herein are for description and not limitation.

The objects of the invention have been well satisfied. These advantages and others will become more fully apparent from the following detailed description when read in conjunction with the accompanying drawings.

DETAILED DESCRIPTION

While the methods and apparatus of the present invention are capable of being used in different applications, a description of a preferred form of apparatus will be given. The present invention comprises a calorimeter having a novel method of heater control and foam detector means. Absent the method of heater control and the foam detector, the general configuration of the test apparatus of the calorimeter of the present invention is known in the art. In particular, the teachings of Fauske's U.S. Pat. No. 5,229,075 are herein incorporated by reference for purposes of describing the preferred test apparatus configuration, absent the method of heater control and foam detector, of the preferred embodiment of the present invention.

Figure 1:
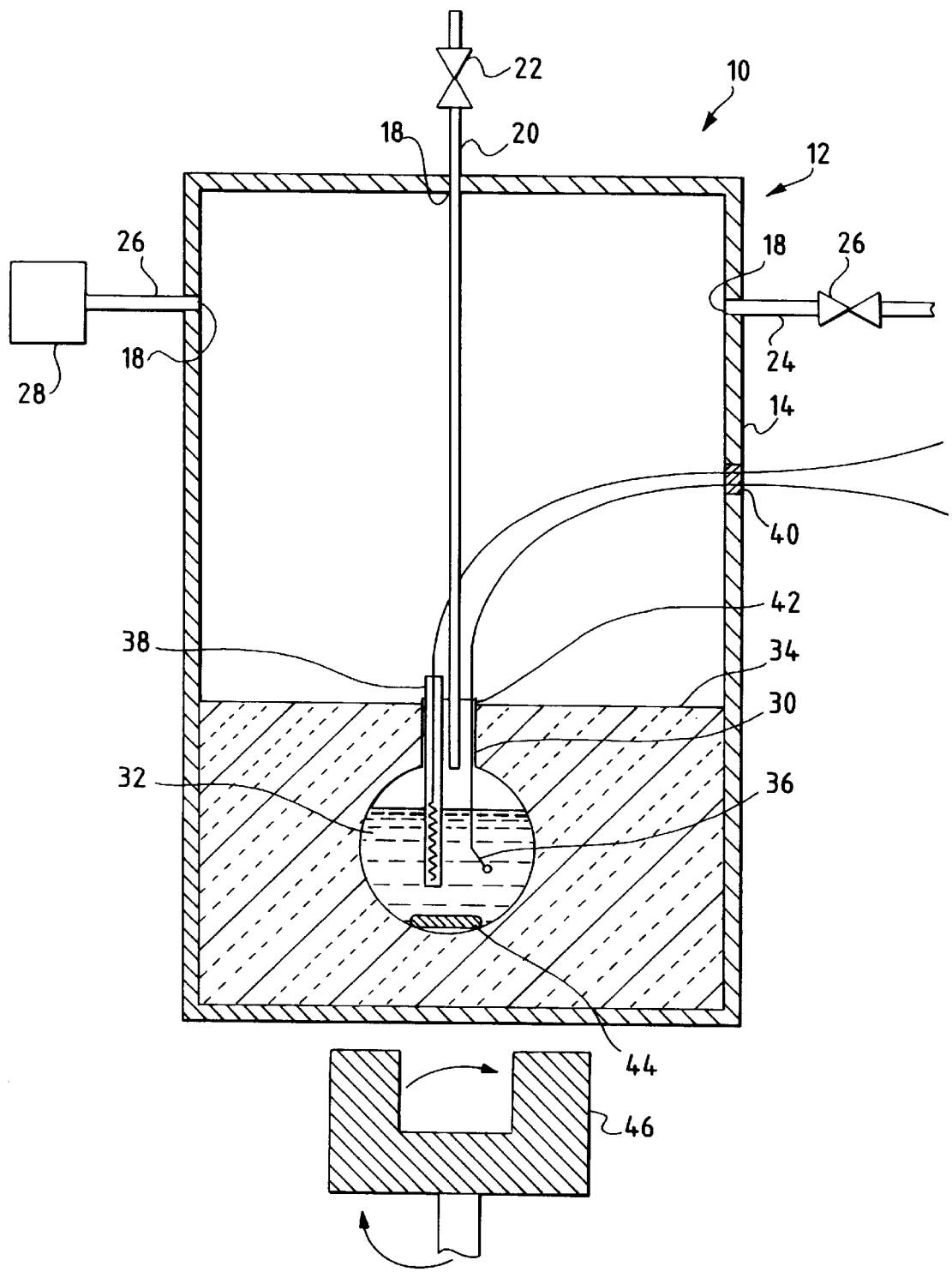
FIG. 1 is a cross section of the preferred test vessel configuration of the invention.

Referring now to the drawings, FIG. 1 shows a test apparatus 10 for carrying out the method of present invention as generally described by Fauske's '075 patent. As shown, the apparatus 10 includes an exterior containment vessel 12 with walls 14. Containment vessel 12 is sealable to insure pressure tightness of the interior. Suitable openings 18 are provided respectively in one or more of the walls 14 for passage of a fill pipe 20 with valve 22, atmosphere control pipe 24 with valve 26, and a pressure measurement pipe 26 with pressure measurement means 28. Preferred pressure measurement means 28 comprise a common commercial strain gage pressure transducer as is available from the Ashcroft Co. Atmosphere control pipe 24 with valve 26 may be connected to a isolatable vent source and/or an isolatable pad gas source, and may be useful to control the pressure in vessel 12 interior, as may be desirable to perform various relief system design experiments, as is explained at length in Fauske's '075 patent.

Test cell 30 contains the test sample material 32. Preferred test cell 30 is comprised of thin glass and is generally spherical in nature, with an open top neck for introduction of material. As taught by Fauske's '075 patent, it is preferred that the thermal mass of test cell 30 be low in comparison to the thermal mass of test material 32, where thermal mass is defined as mass multiplied by specific heat. The ratio of thermal mass of test cell 30 to test material 32 is preferably less than 1:6; is more preferably less than 1:8; and is most preferably less than 1:10. These ratios insure a minimal heat sink effect of test cell 30 on test material 32 as it reacts and generates heat. As explained in detail in Fauske's '075 patent, these ratios insure a "phi factor" that is comparable to that which occurs on an industrial chemical process scale, and thus allows for data from the apparatus of the invention to be applied directly to an industrial process scale.

To further help minimize heat losses, test cell 30 is surrounded by insulating material 34, which may preferably comprises glass fiber insulation or other materials with good thermal insulating properties. Temperature probe 36 is immersed directly in test material 32 to measure the temperature thereof Temperature probe 36 preferably comprises a stainless steel type K thermocouple with a mini connector, but may also comprise a glass coated probe or metal alloy material as may be required for test material 32 compatibility. Shaft diameter for probe 36 is preferably 3/16" or less to insure rapid response to temperature change.

Test material 32 is heated using heater 38, which preferably comprises an electrical resistance coil contained in a glass sheath. Other heaters could be used, for example electrical resistors contained in a flat foil wrap which is attached to the exterior of test cell 30. Heater 38 is preferably powered by a DC power supply. Temperature probe 34 and heater 38 send and receive signals through vessel wall 14 at gland 40. Temperature probe 34 and heater 38 are attached to test cell 30 at its top rim 42. Material may be conveniently introduced to test cell 30 through fill line 20. Agitation of test sample material 30 is provided by magnetic stir bar 44 which spins in cooperation with spinning magnet 46 located external to vessel 10.

Figure 2:
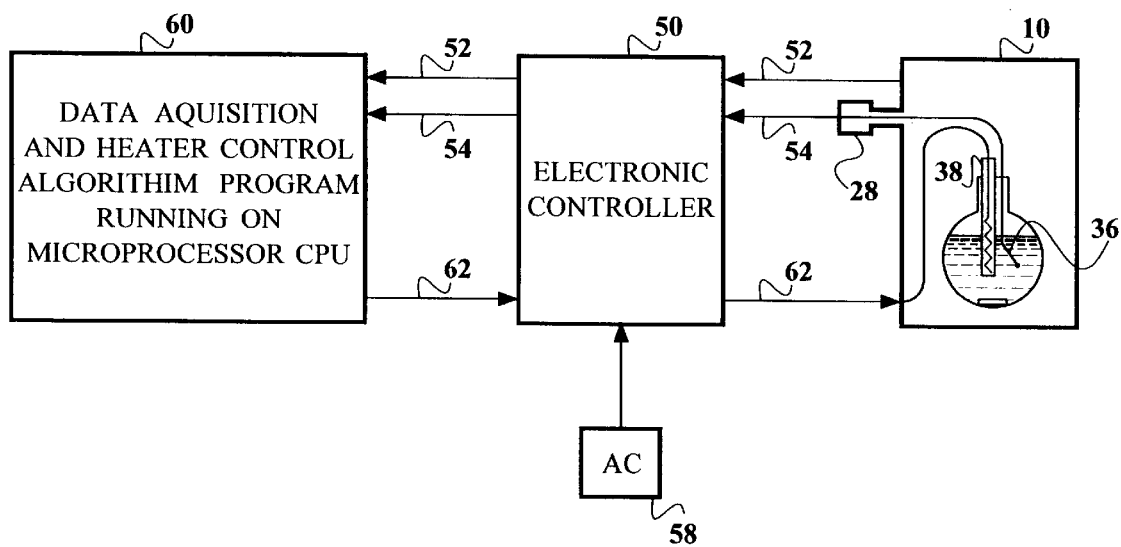
FIG. 2 is a block diagram of a preferred overall apparatus of the invention.

FIG. 2 shows the general configuration of the apparatus of the invention. Vessel 10 is connected to electronic controller 50. Electronic controller 50 provides a heater power supply, and temperature and pressure signal amplifiers and power supplies as may be required. Connection 52 relays temperature data from probe 36 to controller 50, connection 54 relays pressure data from pressure transducer 28, and connection 56 relays heater power from controller 50 to vessel 10 and its heater 38. Connections 52, 54, and 56 are preferably made using insulated cables and connectors as are known in the art and widely commercially available. Electronic controller 50 is powered by a standard 110 V AC power source 58.

Figure 3:
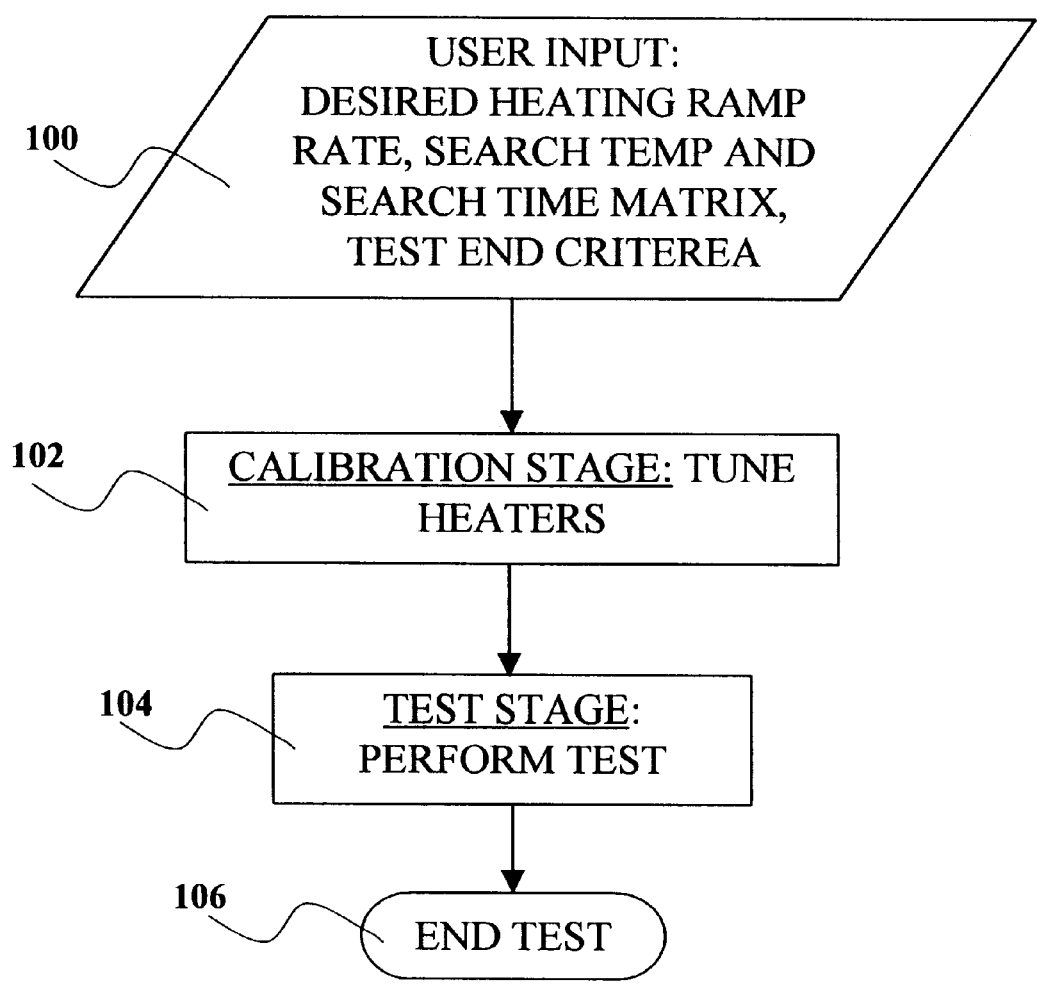
FIG. 3 is a general logic flow chart of a preferred method of heater control of the invention.

The preferred data acquisition and method of heater control comprise a computer program running on microprocessor based microcomputer 60. Microcomputer 60 is connected via connections 52, and 54, to receive temperature and pressure data respectively from controller 50. Connection 62 relays a heater control signal from the method of heater control of the invention running on microcomputer 60 to controller 50. The novel preferred heater control method of the present invention that satisfies the several unresolved needs as discussed infra is generally depicted in FIG. 3 in a logic flowchart. In its preferred form, the control algorithm comprises a computer program for running on a microprocessor based microcomputer. User input 100 is obtained including a matrix of desired search temperatures and search times which correspond to temperatures at which an exotherm will be searched for, times for which a search will be performed, desired ramp rate, and test end criteria. At calibration stage 102, the heater control method tunes the heater for the particular test sample at hand. Through this calibration, the heater is tuned to perform with the particular test sample mass, test sample specific heat, and specific heat loss model that will be encountered during the test at hand.

The calibration stage generally comprises a sequence of ramping the sample temperature followed by holding the sample adiabatic. It is desirable that the calibration sequence be carried out within a temperature space where the test sample is non-reactive so that no reaction heat is evolved. During each ramp and adiabatic interval a proportional integral derivative tuning (PID) mechanism tunes the heater to achieve the desired ramp rate or adiabatic condition with precision. Once satisfactorily tuned, a pair of temperature and heater power coordinates are recorded.

After a sufficient number of respective ramping and adiabatic intervals have been performed, respective polynomial equations are derived for each adiabatic and ramping heater control that relate temperature to heater power. The respective equations are solved for using the respective coordinate pairs of temperature and heater power collected during the calibration stage ramping and adiabatic intervals.

Figure 4:
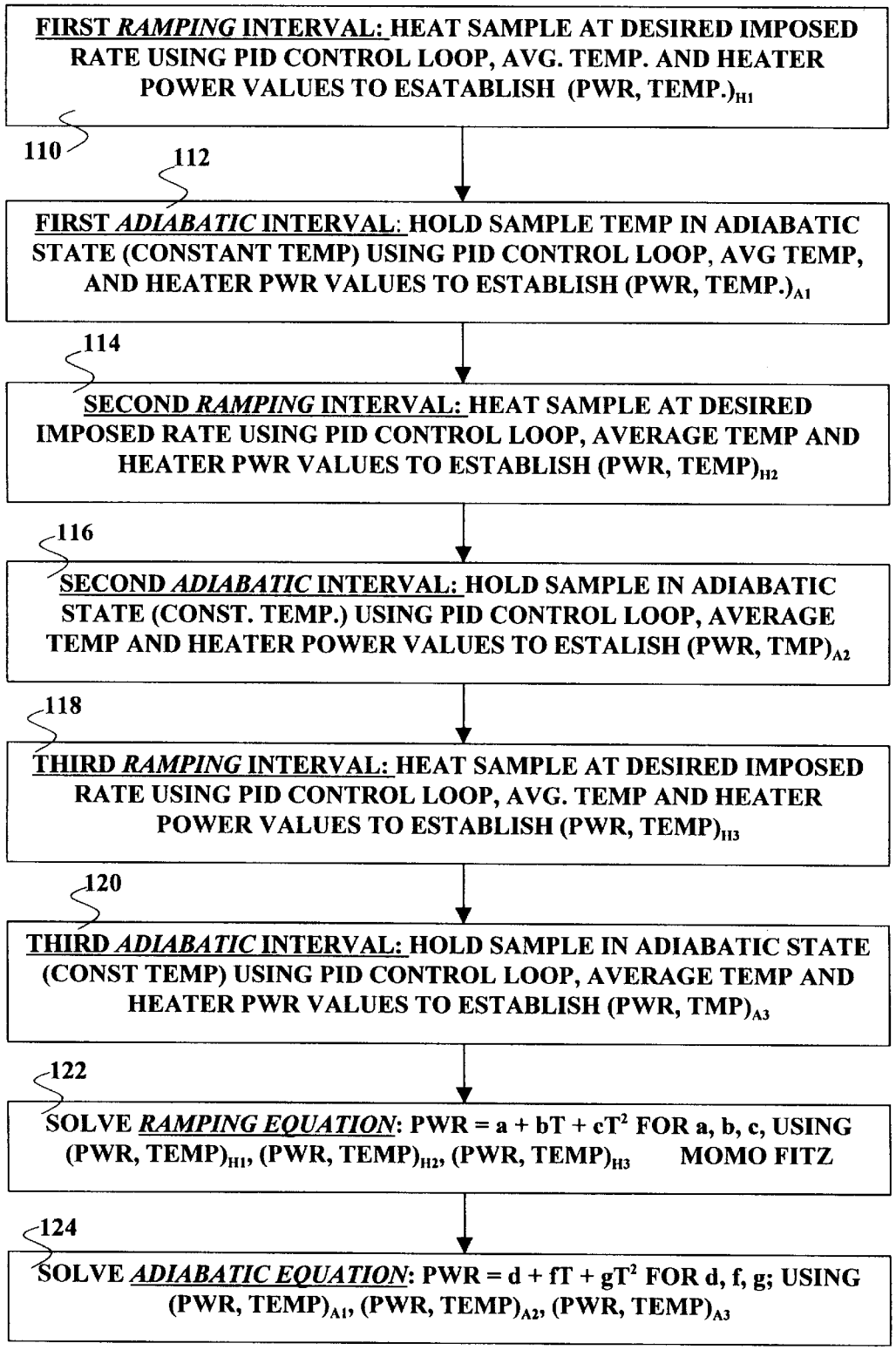
FIG. 4 is a logic flow chart of a preferred calibration stage of the method of heater control of the present invention.

The calibration stage of the preferred heater control method of the present invention is shown in logic diagram FIG. 4. A first ramping interval 110 is begun. After successful tuning, a single coordinate pair of averaged temperature and heater power values are recorded. A first adiabatic interval 112 is then begun. Again, after successful tuning, a single pair of averaged temperature and heater power values are recorded. A second ramping interval 114 is then begun, followed in succession by a second adiabatic interval 116, a third ramping interval 118, and a third adiabatic interval 120, with a stored pair of power and temperature coordinates after each interval.

Figure 5:
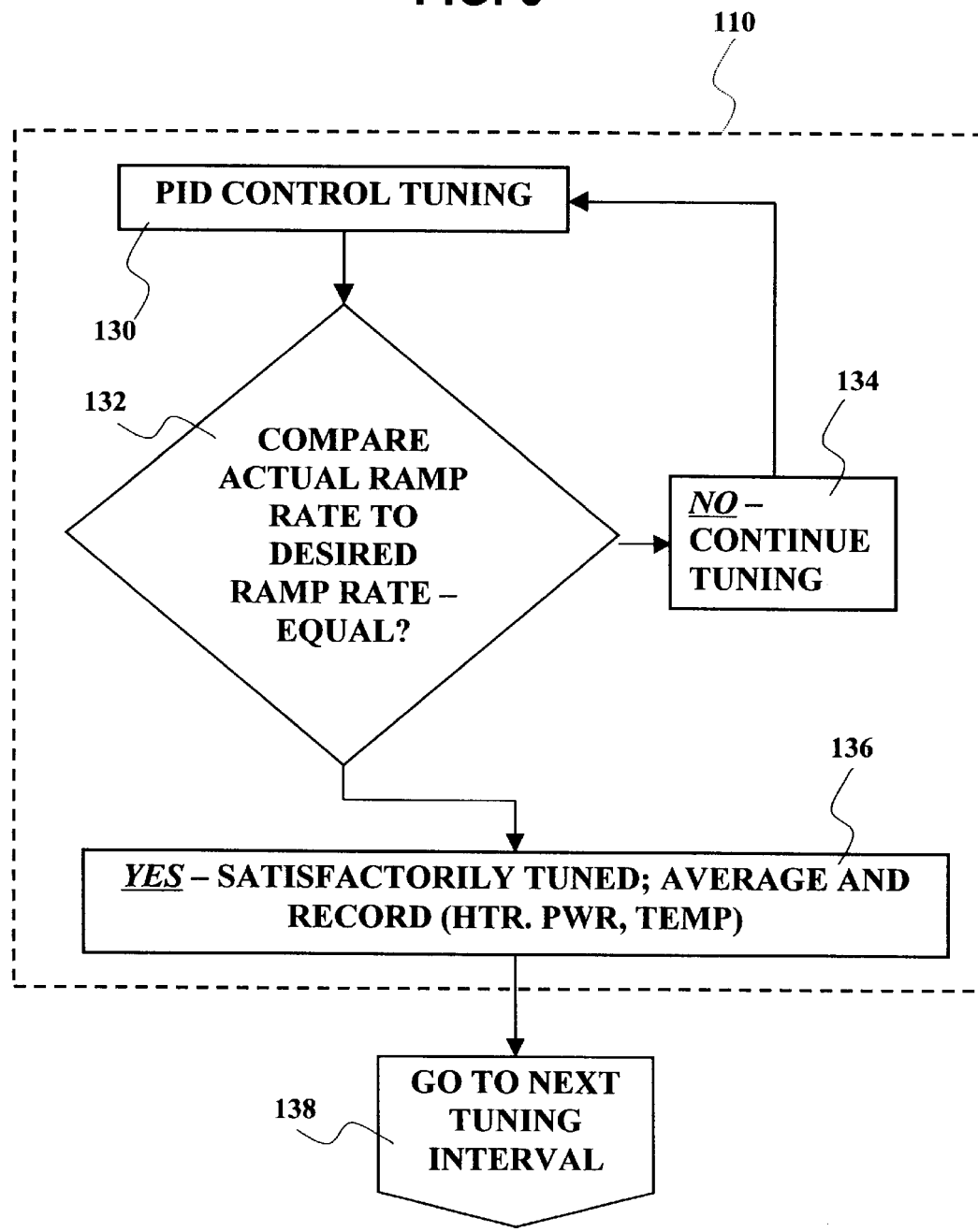
FIG. 5 is a logic flow chart of a preferred individual ramp rate tuning interval of the method of heater control of the present invention.

FIG. 5 shows an individual Ramp Rate Tuning Interval 110, as generally depicted in FIG. 4. After PID tuning 130, the ramp rate achieved is compared to that desired at 132, with a decision made as to whether continue tuning 134, or to determine that tuning has been successful. If successful, coordinate temperature and heater power pairs are begun to be averaged, and a single averaged coordinate pair recorded 136. The program then advances to the next interval 138.

Figure 6:
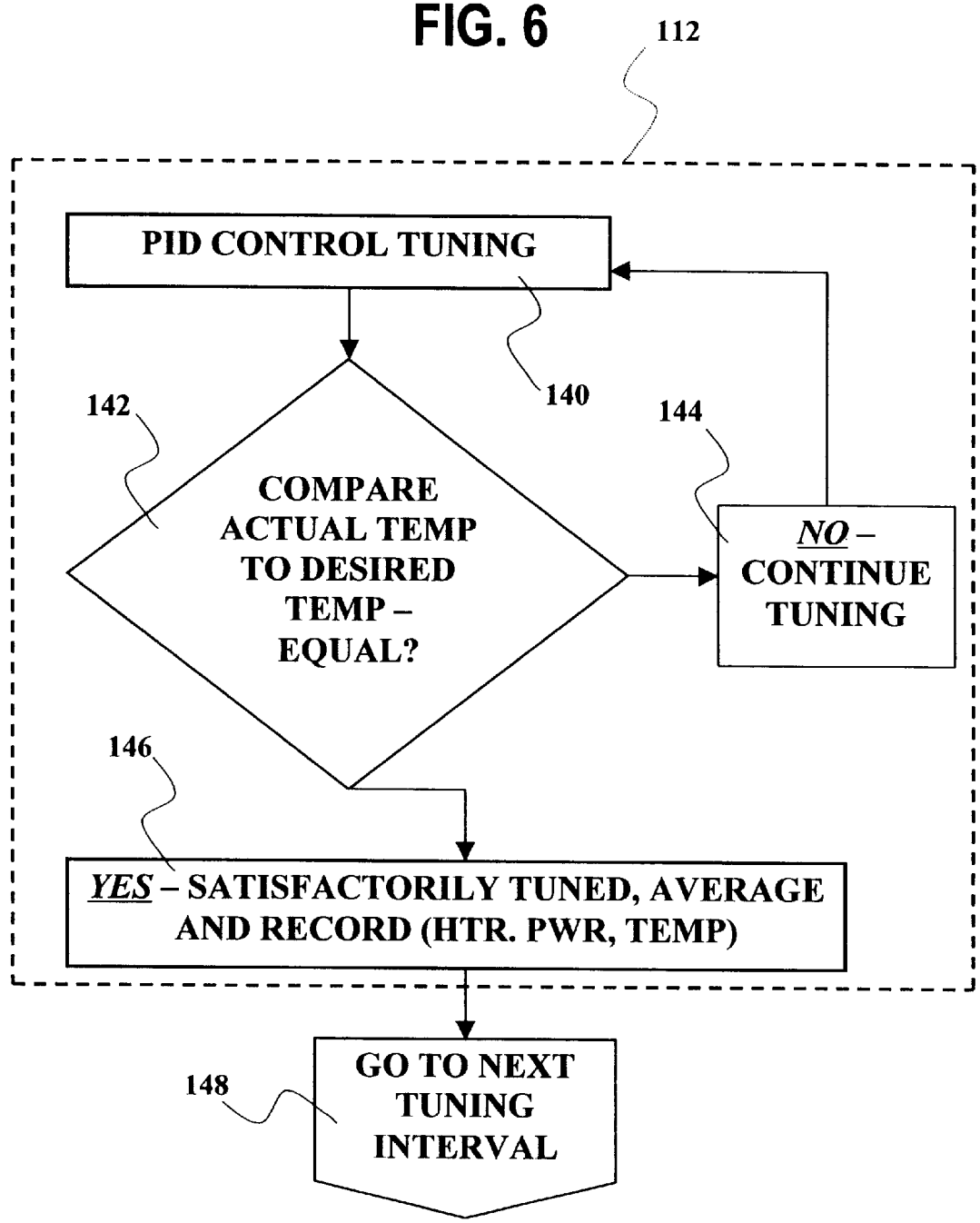
FIG. 6 is a logic flow chart of a preferred individual adiabatic tuning interval of the method of heater control of the present invention.

FIG. 6 shows corresponding logic for a single Adiabatic Tuning Interval 112, as generally depicted in FIG. 4. It is noted that because the sample is non-reactive during the calibration stage, keeping the sample adiabatic equates to holding it at constant temperature. A PID tuning loop 140 is performed to tune the heater to maintain constant temperature in the non-reactive sample, followed by a decision 142 as to whether the sample has reached a steady state of constant temperature and thereby successful completion of tuning. If not yet successful, more tuning is performed 144. If the tuning is successful, coordinates of temperature and heater power are begun to be averaged, with a final single average coordinate pair recorded 146. After completion, the program proceeds to the next interval 148.

Referring once again to FIG. 4, at the completion of the intervals, a mathematical relation is derived relating heater power to temperature required to achieve the desired ramp rate 122 and the adiabatic state 124. The preferred mathematical relation is in the form of a polynomial equation:

$$Htr.Pwr. = a + bT + cT^2$$

with polynomial coefficients a, b, and c that may be solved for using the recorded temperature verses heater power coordinates from the individual calibration intervals. These respective polynomial equations will be used to control the heater during the test stage of the heater control method, and represent a precise approximation of the particular test sample mass, specific heat, and heat loss model to be encountered during the test.

It is noted that the number of respective calibration intervals may be any number larger than 2, with at least three preferred. As the number of respective intervals run increases, a higher order polynomial may be derived. Experience has shown that three intervals, with a resultant $2^{nd}$ order polynomial, provide a useful basis. It is further noted that it is not important what sequence the intervals are performed in.

The tuning performed in the calibration stage of the heater control method of the invention results in greatly improved heater performance over prior art devices that relied on a stored calibration scheme that assumed sample mass, specific heat, and heat loss model. In a series of tests using a non-reactive sample performed to compare the capabilities of the heater control method of the present invention to that of the prior art as described in Fauske's '075, the following results were obtained:

| Desired Ramp Rate: | Imposed Back Pressure: | Rate Achieved Using Fauske '075 Heater Control: | Rate Achieved Using Present Invention Heater Control: |
|---|---|---|---|
| 0.25° C./min. | 0 PSIG | 0.79° C./min. | 0.25° C./min. |
| 0.25° C./min. | 300 PSIG | 0.43° C./min. | 0.25° C./min. |
| 0.60° C./min. | 0 PSIG | 1.10° C./min. | 0.50° C./min. |
| 0.50° C./min. | 300 PSIG | 0.50° C./min. | 0.50° C./min. |

These results clearly demonstrate the advantages of the present invention, particularly under lower back pressures.

Referring once again to FIG. 3, after tuning the heater at calibration stage 102, the control algorithm performs the actual test at 104. The test is continued until user input test end criteria are satisfied, when the test is ended at 106. Test end criteria may include a maximum temperature, pressure, time, observed rate data, or other criteria. The test stage comprises two distinct modes; the ramping mode and the adiabatic mode. In the ramping mode, the heater is driven to raise the test sample temperature. In the adiabatic mode, the heater is driven to balance heat losses from the cell, and to thereby hold the sample adiabatic. The general logic of the testing stage is to heat the sample using the ramping mode to a search temperature where the sample is held adiabatic to search for an exothermic reaction. This process of heating and searching is repeated through a region of interest until a reaction is detected. Once detected, the sample remains under adiabatic mode control so that rates measured are adiabatic and do not include background imposed ramp rates that must be subtracted out.

Figure 7:
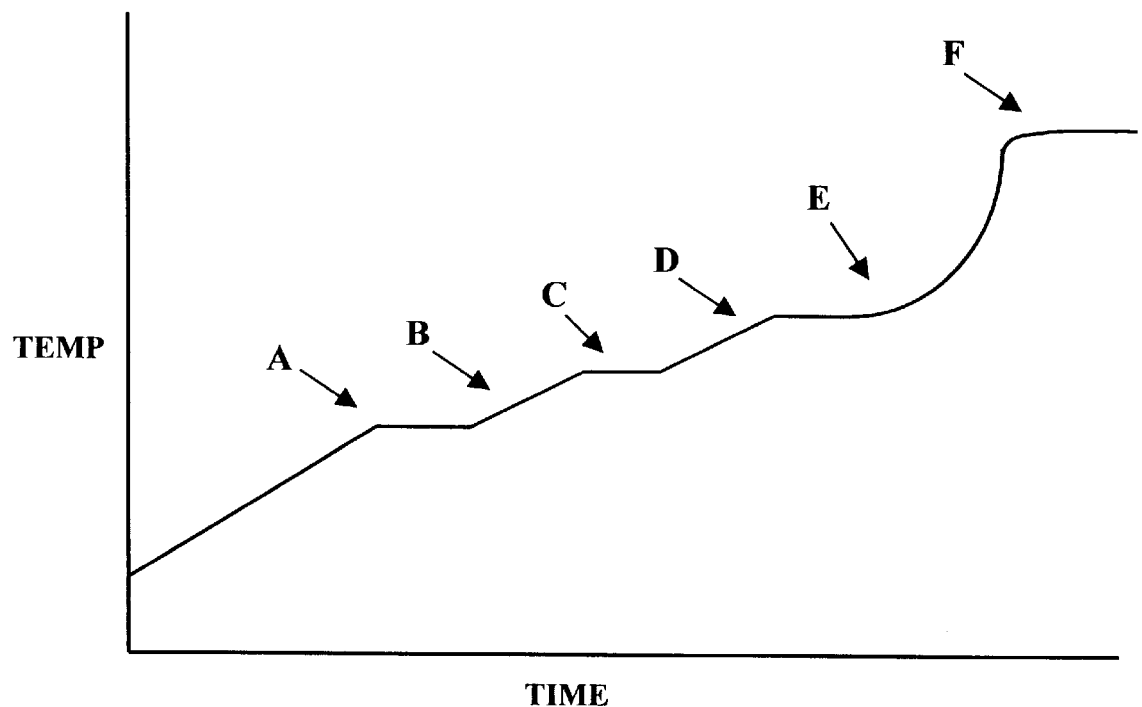
FIG. 7 is a typical plot of data of the preferred apparatus of the present invention in a time versus temperature format.

A plot of time verses temperature history for a sample in the apparatus of the invention under the test stage is shown in FIG. 7. The sample is initially heated from time zero to the first search temperature A. The sample is then held adiabatic for a period of time as input by the user which ends at B. As the temperature did not rise during the adiabatic search interval, the sample is ramped to the next search interval, which begins at C. Again, the adiabatic search interval has not indicated a temperature rise and thus a reaction, the sample is again ramped to D. During this adiabatic search interval, temperature begins to rise at E, indicating the presence of a reaction. The heater will remain in the adiabatic mode to follow the reaction through to completion, which is reached at F. In the heater control methods of the prior art for reaction calorimeters having a single heater and a single temperature probe, adiabatic search intervals were not possible. Thus reactions could only be detected when the rate of reaction had exceeded the input rate. The heater control method of the present invention thereby offers much improved detection of reaction onset.

Figure 8:
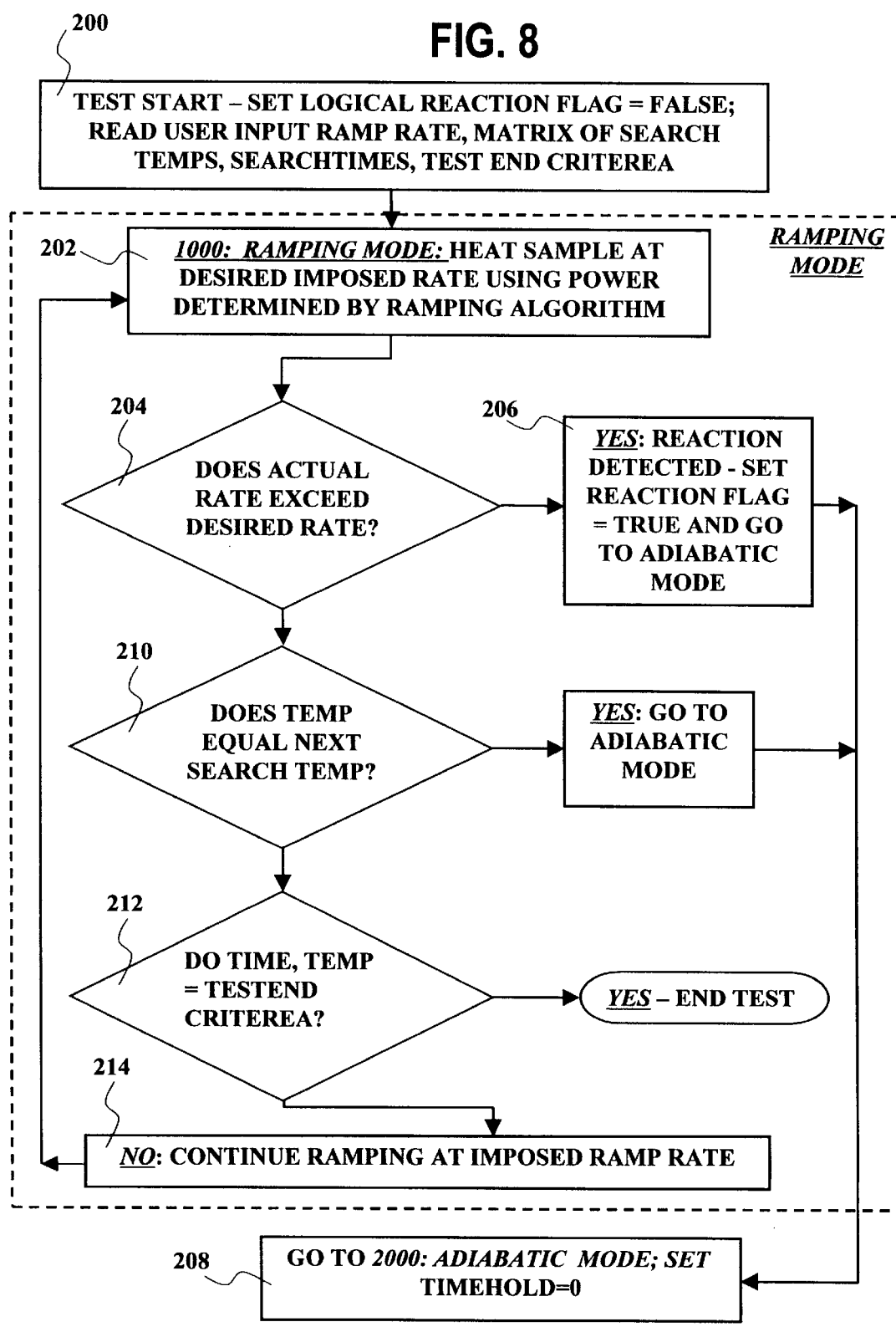
FIG. 8 is a logic flow chart of a preferred ramping mode of the testing stage of the method of heater control of the present invention.

FIG. 8 shows a logic flow chart of the preferred ramping mode of the testing stage of the preferred heater control method of the present invention. From the test start, a number of values 200 are brought into the test mode, including a logical flag indicating the presence of a reaction, a desired ramp rate, a matrix of search temperatures and search times, and criteria under which to shut off the heater and end the test. Module 1000 at 202 calculates a heater power to apply to raise the sample temperature at the desired ramp rate. Module 1000 performs this calculation using the ramping polynomial equation solved for in the calibration stage.

Once ramping has begun, a check 204 is performed to determine if a reaction has been encountered during the ramping. If the actual rate of sample temperature rise is greater than the desired imposed ramp rate, then reaction energy, and hence a reaction, must be present. If so, the logical reaction flag is set 204 to TRUE, and heater control is sent to adiabatic mode 208 to more accurately measure the rate. If the actual temperature rise rate is not greater than the desired ramp rate, a check is made to determine if it is time to begin an adiabatic search interval 210, or to end the test 212. Satisfaction of either of these conditions will end the ramping mode loop. If either condition is not satisfied, the ramping loop continues 214.

Figure 9:
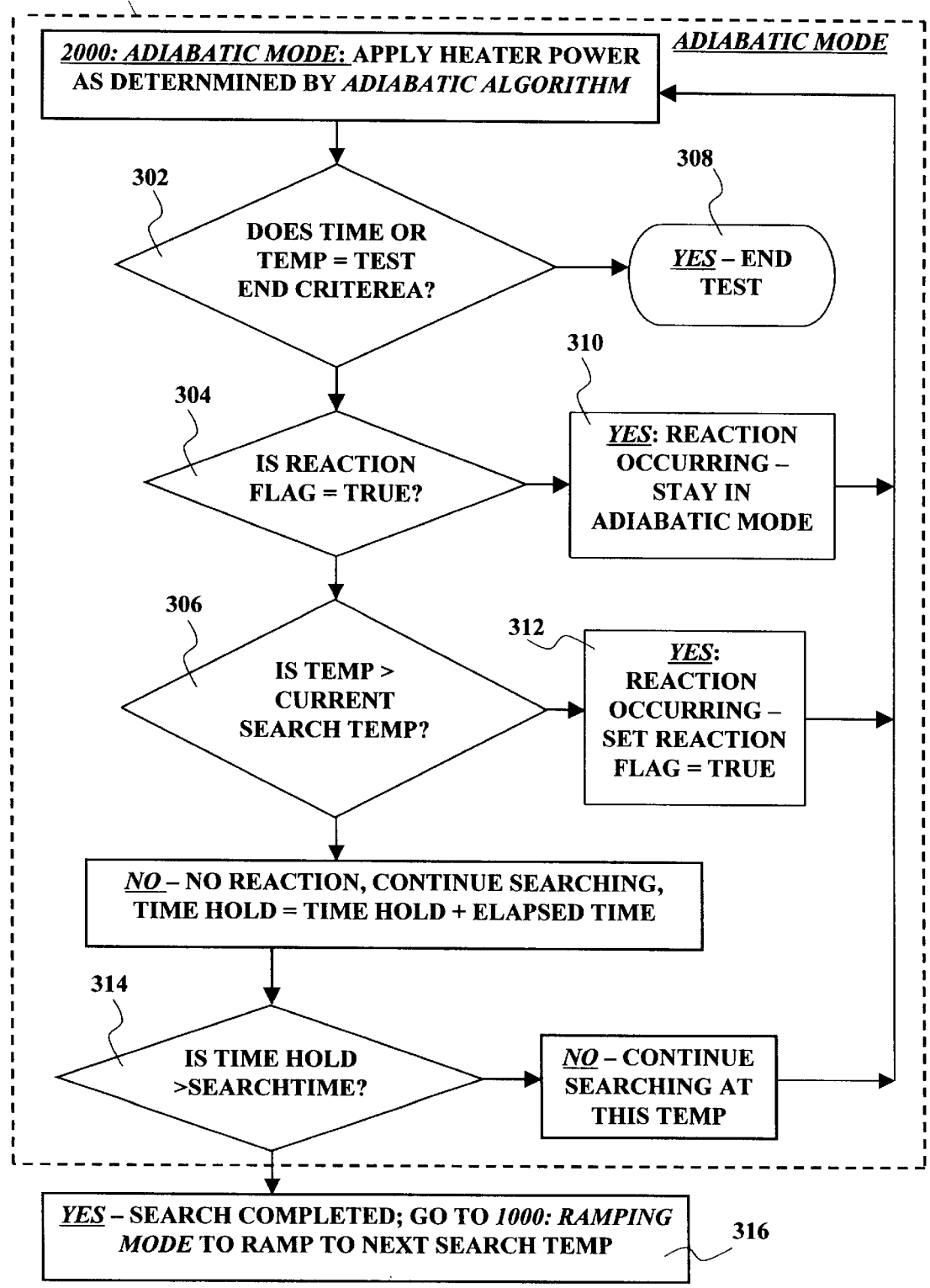
FIG. 9 is a logic flow chart of a preferred adiabatic mode of the testing stage of the method of heater control of the present invention.

A logic flow chart of the adiabatic mode of the testing stage of the preferred heater control method of the invention is shown in FIG. 9. Module 2000 at 300 calculates the amount of heater power required to gold the sample adiabatic using the polynomial adiabatic equation solved for in the calibration stage. After calculating and applying this heater power, the adiabatic mode makes several checks to determine if it is time to end the test 302, if a reaction has already been detected 304, or if a reaction is newly detected 306. Upon the satisfaction the test end criteria, the test is ended; if either of the other conditions are satisfied, the adiabatic mode begins another loop 310, 312, and remains under adiabatic control. If none of these conditions are satisfied, a final check is made 314 to determine whether it is time to ramp to the next adiabatic search interval 316.

Other features or aspects of the heater control method of the present invention may comprise an isothermal mode in which a PID control mechanism maintains constant temperature of the sample regardless of reaction energy. Thus if a reaction should begin to occur, the heater control method will decrease heater power so that reaction energy is used to maintain constant temperature. Under such control, occurrence of a reaction will be indicated by a change in heater power, change in pressure, or change in mass of the sample. The magnitude of reaction energy may be estimated by calibrating the heater power.

Yet another embodiment of the heater control method test stage of the invention comprises a test stage that ramps a sample at a desired constant ramp rate until a reaction is detected, and then goes to an adiabatic mode. Such an embodiment will have the disadvantage over the preferred embodiment of the test stage that reactions may not be detected until the temperature rise rate is greater than the imposed rate, but will have the advantage of being able to perform a test in less time than is required by the preferred test stage.

As discussed infra and in detail in Fauske's 750 patent, the apparatus of the invention finds particular utility as a tool useful for obtaining design basis data for chemical process relief systems.

Figure 10:
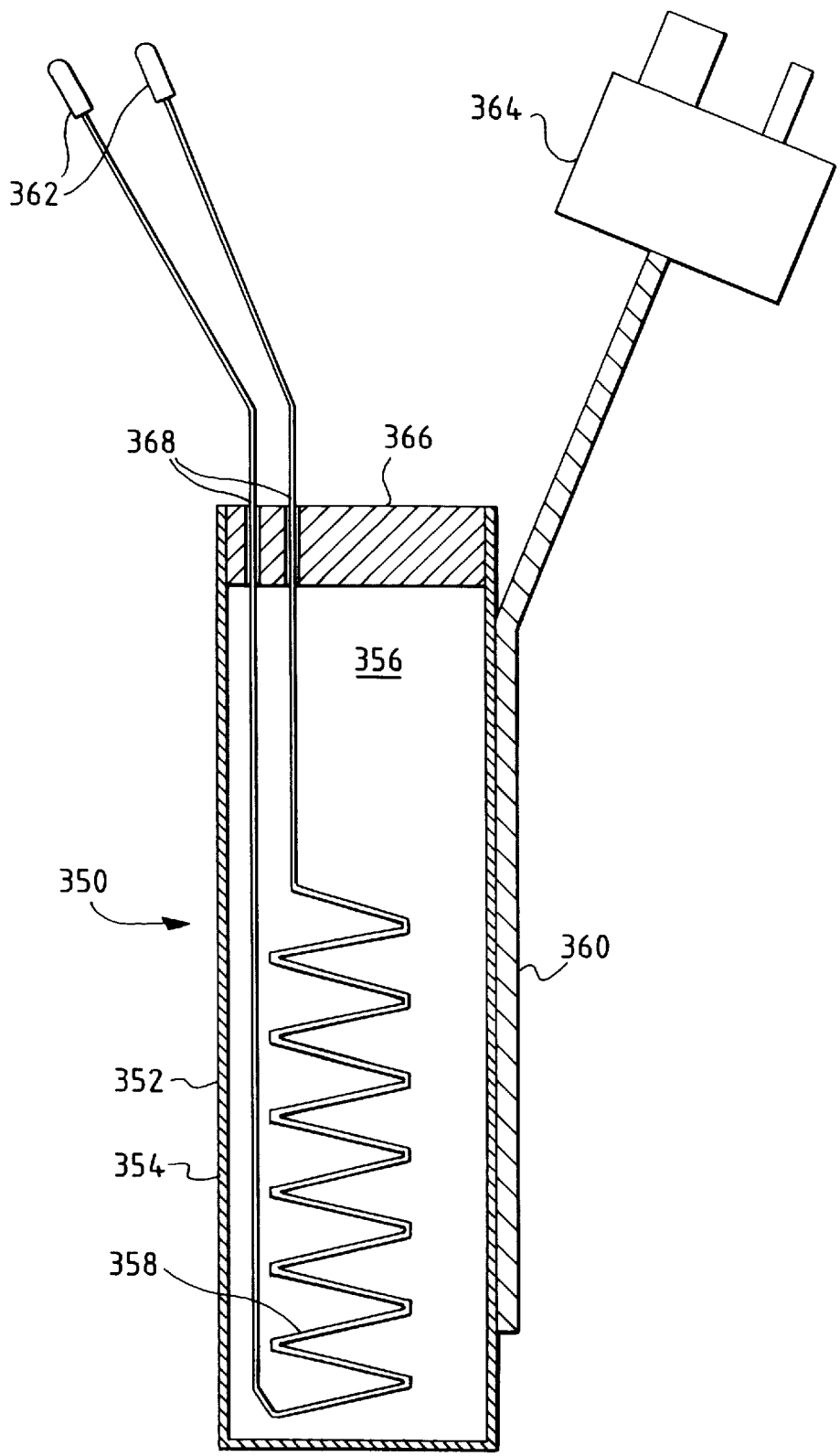
FIG. 10 is a cross sectional view of a preferred foam detector probe of the invention.

The present invention further comprises a foam detector for detecting the presence of foam in a sample being tested in a calorimeter. FIG. 10 shows a preferred foam detector of the present invention. It comprises a cylindrical probe 350 made of glass with thin walls 352 and probe surface 354. The interior 356 of probe 350 contains heater resistor coil 358 for heating walls 352 and probe surface 354. Thermocouple 360 is attached to probe surface 354 to measure surface temperature. Preferred thermocouple 360 is a type K with a stainless steel shaft of no more than $3/16''$ diameter for rapid response to temperature changes. Heater coil 358 is connected to a DC power source via connectors 362; thermocouple 360 likewise connects to a device for reading and recording temperature via connector 364. Connectors 362 and 364 may be of any configuration, many of which are known in the art and commercially available; preferred connectors comprise miniature plug type connectors 362, and a miniature K type thermocouple connector 364. Interior 356 is sealed with plug 366, with pressure fit passages 368 allowing passage of heater coil 358 leads therethrough.

Figure 11A:
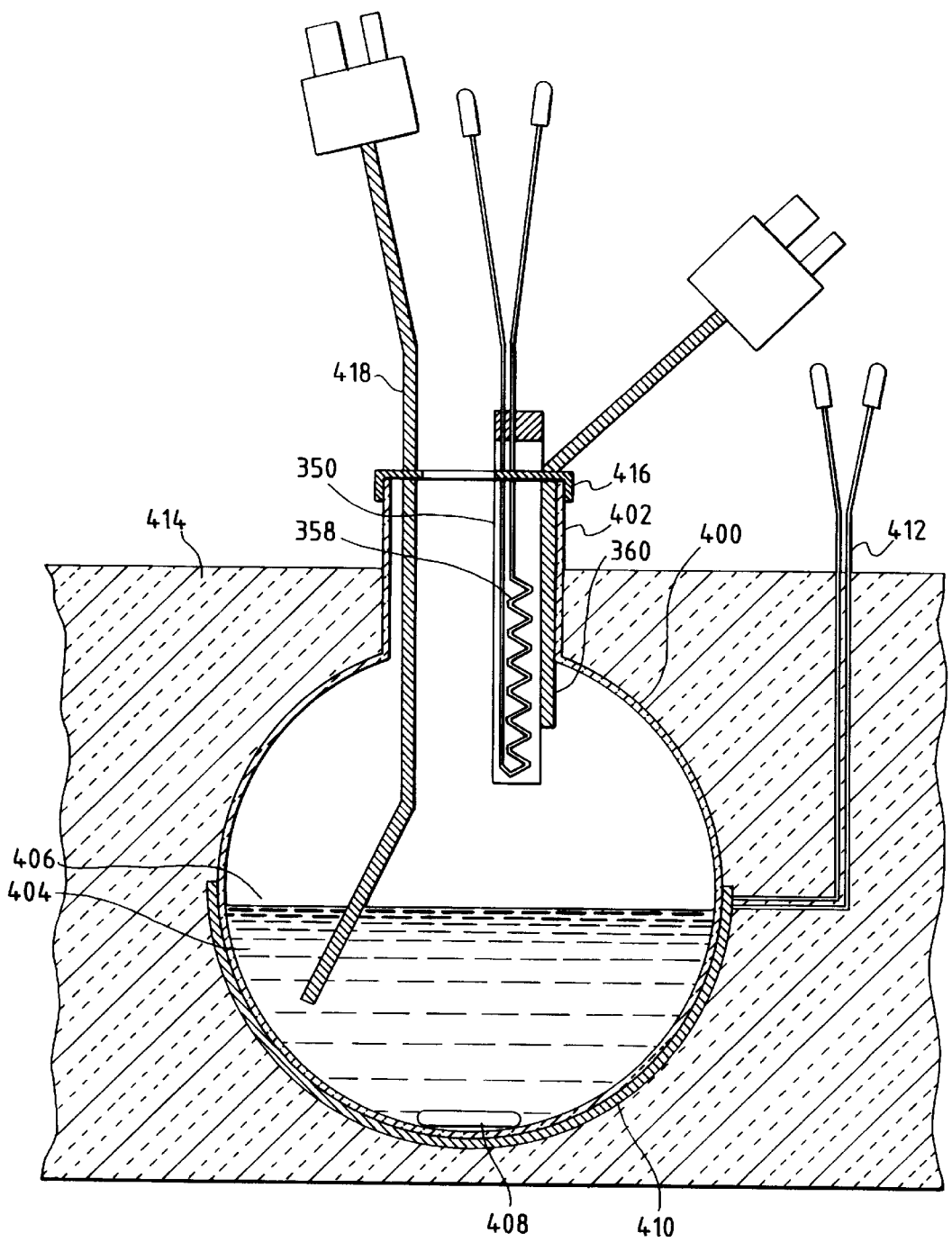
FIGS. 11A and 11B are cross sectional views of the preferred foam detector of the invention in use in the calorimeter of the invention.

FIG. 11A shows a cross sectional view of the preferred foam detector of the invention configured in the preferred test cell configuration as described herein, and as substantially described in Fauske's '750 patent. The present configuration includes spherical test cell 400 with open cylindrical neck 402. Test cell 400 contains test sample liquid 404, with surface 406. Test sample 404 is agitated with magnetic stirrer 408, which is driven by a spinning external magnet (not shown). FIG. 11A shows an external heater 410 for heating the sample, which is an alternate heater to that of FIG. 1. External heater 410 comprises a flat foil wrap surrounding an electrical resistance element. External heater 410 is wrapped about the outside lower surface of test cell 400. External heater 410 has electrical leads 412, which extend through glass fiber insulation 414 which surrounds test cell 400.

Foam detector 350 is located in the open test cell neck 402 and above test sample surface 406. Foam detector is as illustrated in FIG. 10, with heater coils 358 and probe thermocouple 360. Foam detector may be held in place using clip 416 mounted on test cell neck 402.

During a test, test sample 404 is heated using external heater 410 to initiate an exothermic reaction. Sample thermocouple 418 is immersed directly in test sample 404 to measure its temperature. Foam detector 350 is heated with coils 358 such that probe surface temperature as measured by probe thermocouple 360 is substantially in excess of a predetermined tempering temperature of components of test sample 404. For instance, if sample 404 is aqueous, then detector probe surface would be heated to a temperature substantially in excess of 100° C.

Thermocouple 360 sends an output signal to any suitable device for converting, displaying, and/or recording as is generally well known in the art. Power for heater coil 358 is preferably DC, and may be supplied in any manner as is known in the art. An AC/DC converter may, for instance, be connected in sequence with a variable resistor and an AC power supply, with the resistor being manually adjusted until probe surface temperature as indicated by thermocouple 360 reaches its desired level. Alternatively, a controller circuit may be constructed that automatically powers heater coil 358 based on an input set temperature, with that set temperature being compared to thermocouple 360 reading which may be input to the controller. The preferred foam detector of the present invention will have heater power supply and thermocouple signal conditioning in the same electronic controller as is used to condition test sample thermocouple and power test sample heater, with automated control of the probe heater and data acquisition performed by a control algorithm running on the same microprocessor based computer as is used for the calorimeter of the invention.

Figure 11B:
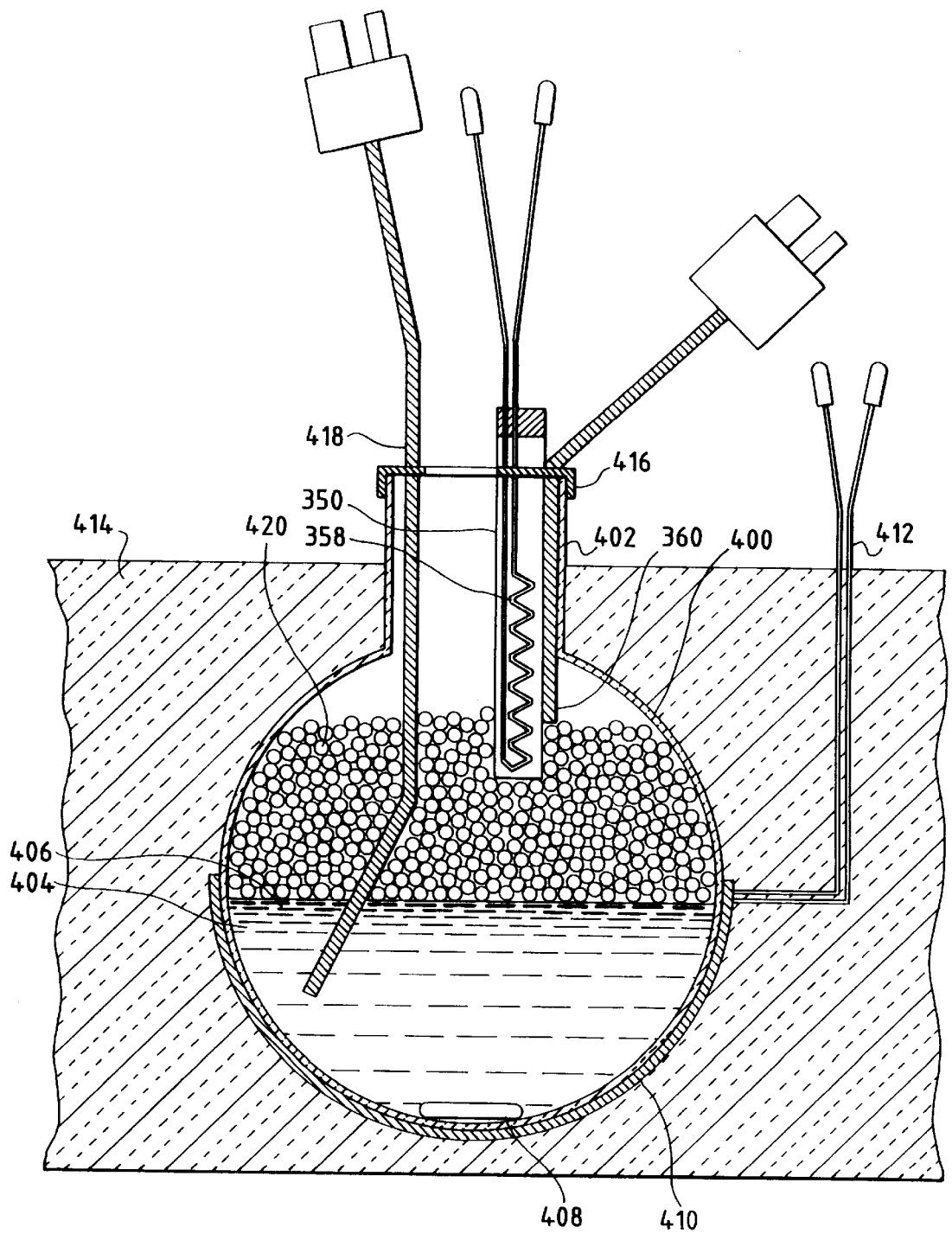

FIG. 11B illustrates the configuration of FIG. 11A as foaming occurs and foam 420 comes into contact with probe 350. As the liquid component of foam 420 comes into contact with the surface of probe 350 which is at a temperature substantially in excess of the tempering temperature of that liquid component, the liquid begins to boil. As boiling occurs, energy corresponding to the latent heat of vaporization of the liquid is drawn from the probe. The surface temperature of the probe drops to the tempering temperature of the liquid, indicating foam presence. Temperature of the liquid test sample at this point as indicated by sample thermocouple 418 will indicate at what temperature the sample evolved foam.

Foam detector 350 should be of limited thermal capacity so that its temperature will quickly respond to contact with the liquid foam component cooling media.

Figure 12:
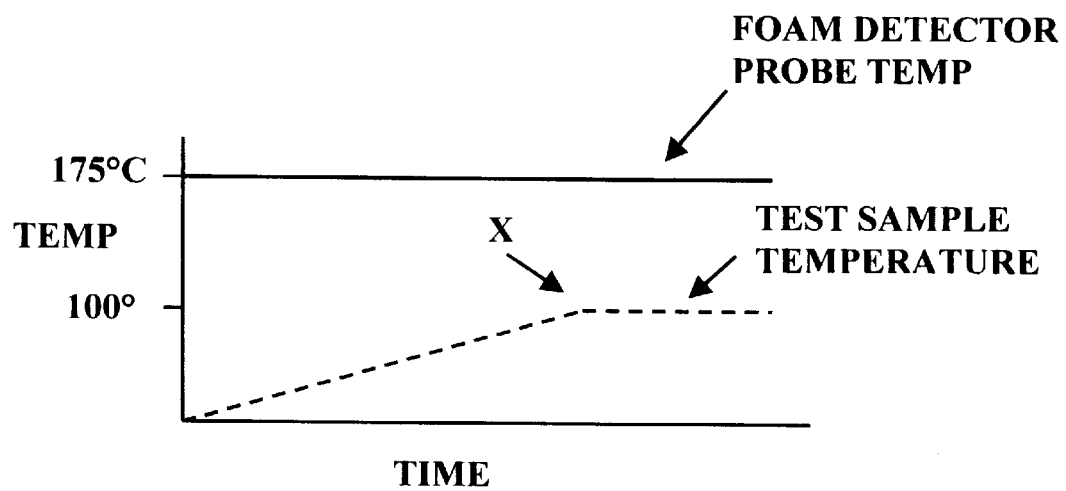
FIGS. 12 and 13 are data plots displaying data from the preferred foam detector of the invention.
Figure 13:
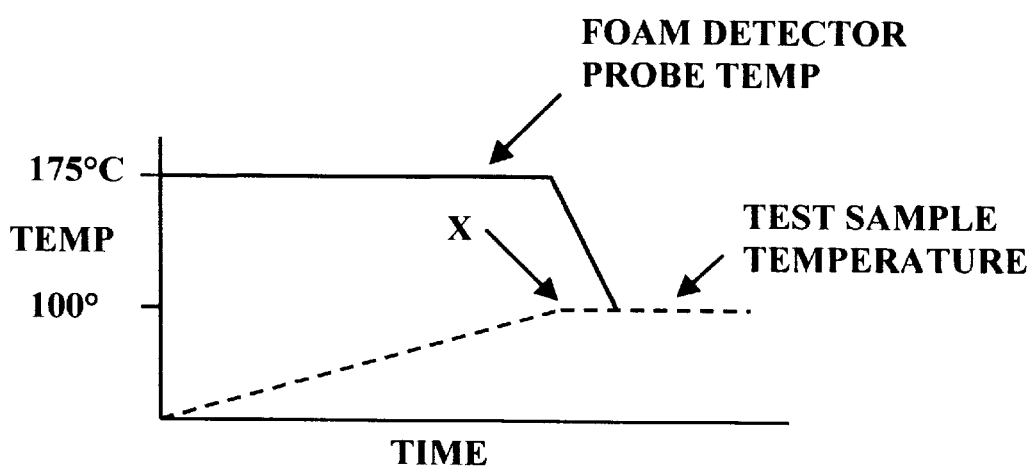

By way of example, FIGS. 12 and 13 show data plots resulting from the preferred foam detector of the invention, with 12 showing a non-foamy mixture of water being heated under atmospheric pressure, and 13 showing a foamy water with soap mixture. In FIG. 12, the foam detector probe is heated to a temperature of 175° C., which is substantially in excess of water's tempering temperature of 100° C. The water sample is heated using the sample heater until it reaches 100° C., as indicated by point X in FIG. 12, at which point the sample temperature becomes constant as water vaporizes. Foam detector temperature does not change at this point, indicating that no foam is present. In FIG. 13's plot for a soapy water solution, on the other hand, as boiling begins at 100° C., indicated by point X of FIG. 13, foam detector probe temperature quickly falls from its original temperature of 175° C. to 100° C. This occurs as the water component of the foam hits the detector probe and boils, sapping the probe of heat energy which is transferred into latent heat of vaporization energy.

Thus the foam detector of the invention indicates the presence of foam, and the temperature at which foamy behavior began to occur. This information may be used to great advantage for designers of process relief systems.

Other embodiments of the foam detector of the invention may comprise metal heated metal elements with a temperature measurement probe attached that operates in the same general manner as the preferred foam detector. Still other embodiments of the foam detector of the invention may comprise probes that detect contact with foam by means other than cooling, such as by measuring a change in electrical conductivity as foam contacts conductors.

The advantages of the disclosed invention are thus attained in an economical, practical, and facile manner. While preferred embodiments and example configurations have been shown and described, it is to be understood that various further modifications and additional configurations will be apparent to those skilled in the art. It is intended that the specific embodiments and configurations herein disclosed are illustrative of the preferred and best modes for practicing the invention, and should not be interpreted as limitations on the scope of the invention as defined by the appended claims.

What is claimed is:

1. An improved heater control method for a calorimeter apparatus, the calorimeter of the type having an exterior containment vessel, a test cell containing a particular test sample, temperature measurement means for measuring the test sample temperature, heating means for heating the test sample, data acquisition means for recording data, wherein particular test conditions comprise particular test sample mass, particular test sample specific heat, and a particular test sample heat loss model; the improvement comprising a method for heater control during a test, the method comprising:

a) initiating a test run with the particular test sample; tuning the heater means in an initial calibration stage to the particular test conditions, said calibration stage having a control loop to tune said heater, said calibration stage determining a heater control equation relating temperature to heater power;

b) controlling said heater in a subsequent test stage during said test run with the particular test sample, said test stage using said heater control equation to calculate heater power to be applied; and c) said calibration stage having at least two temperature ramping intervals and at least two adiabatic holding intervals, said calibration stage determining a heater ramping control equation and a heater adiabatic control equation, and d) said test stage controls said heating means with said ramping control equation to ramp the sample temperature until an exothermic reaction is detected, and said test stage controls said heating means with said adiabatic control equation to hold the sample adiabatic after an exothermic reaction has been detected.

2. An improved heater control method for a calorimeter apparatus, the calorimeter of the type having an exterior containment vessel, a test cell containing a particular test sample, temperature measurement means for measuring the test sample temperature, heating means for heating the test sample, data acquisition means for recording data, wherein particular test conditions comprise particular test sample mass, particular test sample specific heat, and a particular test sample heat loss model; the improvement comprising a method for heater control during a test, the method comprising:

a) initiating a test run with the particular test sample; tuning the heater means in an initial calibration stage to the particular test conditions, said calibration stage having a control loop to tune said heater, said calibration stage determining a heater control equation relating temperature to heater power;

b) controlling said heater in a subsequent test stage during said test run with the particular test sample, said test stage using said heater control equation to calculate heater power to be applied; and c) said calibration stage having at least two temperature ramping intervals and at least two adiabatic holding intervals, said calibration stage determining a ramping polynomial control equation for use in ramping the sample, said calibration stage determining an adiabatic polynomial control equation for holding the sample in an approximate adiabatic state; and d) said test stage sequentially and repeatedly ramping said sample using said ramping polynomial control equation, and holding said sample adiabatic using said adiabatic control equation to search for an exothermic reaction, and said test stage holding said sample in an adiabatic state after an exothermic reaction has been detected.

3. An improved heater control method for a calorimeter apparatus, the calorimeter of the type having an exterior containment vessel, a test cell containing a particular test sample, temperature measurement means for measuring the test sample temperature, heating means for heating the test sample, data acquisition means for recording data, wherein particular test conditions comprise particular test sample mass, particular test sample specific heat, and a particular test sample heat loss model; the improvement comprising a method for heater control during a test the method comprising:

a) initiating a test run with the particular test sample; tuning the heater means in an initial calibration stage to the particular test conditions, said calibration stage having a control loop to tune said heater, said calibration stage determining a heater control equation relating temperature to heater power;

b) controlling said heater in a subsequent test stage during said test run with the particular test sample, said test stage using said heater control equation to calculate heater power to be applied; and c) further comprising foam detector means.

4. An improved heater control method as in claim 3, the test sample having a liquid surface, wherein said foam detector comprises a probe for indicating contact with foam, said probe placed above the surface level of the test sample.

5. An improved heater control method as in claim 4, wherein the test sample material has a tempering temperature, and wherein:

a) said foam detector probe having a probe surface, having a heater for heating said probe surface to a temperature substantially exceeding the test sample tempering temperature;

b) said foam detector probe having temperature measurement means attached to said probe surface for indicating said surface temperature; said temperature measurement means generating a signal, means for supplying power to said heater, means for receiving and reading said temperature signal; and c) said foam detector probe indicating contact with foam when foam comes into contact with said heated probe surface which is thereby cooled.

6. An improved heater control method as in claim 5, wherein:

a) the test cell is spherical with an open cylindrical neck having an interior;

b) said detector probe comprises a thin walled glass cylinder, having coiled electrical resistor heater within it for heating said probe surface, having a thermocouple attached to said probe surface for measuring surface temperature;

c) said detector probe placed above the test sample surface in said cell open neck interior; and d) said detector probe indicating contact with foam when said foam comes into contact with said probe surface thereby cooling it.

7. A calorimeter apparatus having a test sample with a tempering temperature, where thermal mass is equal to mass multiplied by specific heat, and where test conditions include sample mass, specific heat, and a sample heat loss model, comprising:

a) a sealable containment vessel having pressure detection means;

b) a test cell for containing the test sample, said cell housed within the containment vessel, a ratio of said test cell thermal mass to said test sample thermal mass of less than 1:8, said test cell having thermal insulation;

c) test sample agitation means;

d) a single thermocouple in direct contact with the test sample of measuring sample temperature, e) a single heater for heating the test sample;

f) data acquisition means for recording data;

g) foam detector means comprising a probe having a surface heated to a temperature substantially in excess of the material tempering temperature, having temperature measurement means for measuring the temperature of said probe surface, said surface being quickly cooled when it comes into contact with foam; and h) a heater control sequence comprising:
   i) a calibration stage for tuning said heater to the test conditions, said calibration stage having a control loop to tune said heater to achieve a desired sample ramp rate, said calibration stage having a control loop to tune said heater to achieve a desired sample adiabatic hold, said calibration stage determining a heater ramping control equation and a heater adiabatic control equation; and
   ii) a test stage for controlling said heater during a test, said test stage having a ramping mode using said ramping control equation, and said test stage having an adiabatic mode using said adiabatic control equation.

8. A calorimeter apparatus having a test sample with a surface and a tempering temperature, where thermal mass is equal to mass multiplied by specific heat, and where test conditions include sample mass, specific heat, and a sample heat loss model, comprising:
   a) a sealable containment vessel having pressure detection means;
   b) a test cell for containing the test sample, said cell housed within the containment vessel, a ratio of said test cell thermal mass to said test sample thermal mass of less than 1:8, said test cell having thermal insulation, said test cell being spherical with an open neck having an interior;
   c) test sample agitation means;
   d) a single thermocouple in direct contact with the test sample of measuring sample temperature,
   e) a single heater for heating the test sample;
   f) foam detector means comprising a cylindrical probe having a probe surface heated to a temperature substantially in excess of the material tempering temperature, having a thermocouple for measuring the temperature of said probe surface, said probe surface being quickly cooled when it comes into contact with foam, said probe placed in said test cell neck interior above said test sample surface level;
   g) data acquisition means for recording temperature, pressure, time, heater, and foam detector data; and
   h) a heater control sequence comprising:
      i) a calibration stage for tuning said heater to the test conditions, said calibration stage having a proportional integral derivative control loop to tune said heater to achieve a desired sample ramp rate, said calibration stage having a proportional integral derivative control loop to tune said heater to achieve a desired sample adiabatic hold, said calibration stage determining a heater ramping control polynomial equation and a heater adiabatic control polynomial equation; and
      ii) a test stage for controlling said heater during a test, said test stage having a ramping mode using said ramping control equation, and said test stage having an adiabatic mode using said adiabatic control equation.

9. An improved heater control method for a calorimeter apparatus, the calorimeter of the type having an exterior containment vessel, a test cell containing a test sample, temperature measurement means for measuring the test sample temperature, heating means for heating the test sample, data acquisition means for recording data, wherein test conditions comprise sample mass, sample specific heat, and a sample heat loss model; the improvement comprising a method of heater control comprising:

(a) tuning the heater means in a calibration stage to the test conditions, said calibration stage having a control loop to tune said heater, said calibration stage determining a heater control equation relating temperature to heater power; said calibration stage having at least two temperature ramping intervals and at least two adiabatic holding intervals, said calibration stage determining a heater ramping control equation and a heater adiabatic control equation; and (b) controlling said heater in a test stage during a test, said test stage using said heater control equation to calculate heater power to be applied; wherein said test stage controls said heating means with said ramping control equation to ramp the sample temperature until an exothermic reaction is detected, and said test stage controls said heating means with said adiabatic control equation to hold the sample adiabatic after an exothermic reaction has been detected.

10. An improved heater control method for a calorimeter apparatus, the calorimeter of the type having an exterior containment vessel, a test cell containing a test sample, temperature measurement means for measuring the test sample temperature, heating means for heating the test sample, data acquisition means for recording data, wherein test conditions comprise sample mass, sample specific heat, and a sample heat loss model; the improvement comprising a method of heater control comprising:

a) tuning the heater means in a calibration stage to the test conditions, said calibration stage having a control loop to tune said heater, said calibration stage determining a heater control equation relating temperature to heater power; said calibration stage having at least two temperature ramping intervals and at least two adiabatic holding intervals, said calibration stage determining a ramping polynomial control equation for use in ramping the sample, said calibration stage determining an adiabatic polynomial control equation for holding the sample in an approximate adiabatic state; and b) controlling said heater in a test stage during a test, said test stage using said heater control equation to calculate heater power to be applied; said test stage sequentially and repeatedly ramping said sample using said ramping polynomial control equation, and holding said sample adiabatic using said adiabatic control equation to search for an exothermic reaction, and said test stage holding said sample in an adiabatic state after an exothermic reaction has been detected.

11. An improved heater control method for a calorimeter apparatus, the calorimeter of the type having an exterior containment vessel, a test cell containing a test sample, temperature measurement means for measuring the test sample temperature, heating means for heating the test sample, data acquisition means for recording data, wherein test conditions comprise sample mass, sample specific heat, and a sample heat loss model; the improvement comprising:
   a. a method of heater control comprising:
      (i) tuning the heater means in a calibration stage to the test conditions, said calibration stage having a control loop to tune said heater, said calibration stage determining a heater control equation relating temperature to heater power;
      (ii) controlling said heater in a test stage during a test, said test stage using said heater control equation to calculate heater power to be applied; and
   b. wherein the heater control method further comprises foam detection means.

12. An improved heater control method for a calorimeter apparatus, the calorimeter of the type having an exterior containment vessel, a test cell containing a particular test sample, temperature measurement means for measuring the test sample temperature, heating means for heating the test sample, data acquisition means for recording data, wherein particular test conditions comprise particular test sample mass, particular test sample specific heat, and a particular test sample heat loss model; the improvement comprising a method for heater control during a test, the method comprising:

a) initiating a test run with the particular test sample; tuning the heater means in an initial calibration stage to the particular test conditions, said calibration stage having a control loop to tune said heater, said calibration stage determining a heater control equation relating temperature to heater power; said initial calibration stage comprising at least one ramping interval and at least one holding interval; and b) controlling said heater in a subsequent test stage during said test run with the particular test sample, said test stage using said heater control equation to calculate heater power to be applied; said test stage comprising at least one ramping interval and at least one adiabatic interval.

13. An improved heater control method as in claim 12, wherein the particular test sample undergoes an exothermic reaction during said at least one adiabatic interval during said test stage of said test run, and wherein said heater holding control equation controls the heater to maintain the particular test sample during said exothermic reaction in a substantially adiabatic state.

14. An improved heater control method for a calorimeter apparatus, the calorimeter of the type having an exterior containment vessel, a test cell containing a particular test sample, temperature measurement means for measuring the test sample temperature, heating means for heating the test sample, data acquisition means for recording data, wherein particular test conditions comprise particular test sample mass, particular test sample specific heat, and a particular test sample heat loss model, wherein the test sample undergoes an exothermic reaction; the improvement comprising a method for heater control during a test, the method comprising:

a) initiating a test run with the particular test sample; tuning the heater means in an initial calibration stage to the particular test conditions, said calibration stage having a control loop to tune said heater, said calibration stage determining a heater control equation relating temperature to heater power; and b) controlling said heater in a subsequent test stage during said test run with the particular test sample, said test stage using said heater control equation to calculate heater power to be applied, and wherein said heater control equation controls the heater to maintain the particular test sample in a substantially adiabatic condition while the test sample undergoes an exothermic reaction.

* * * * *